(12) United States Patent
Devisetty et al.

(10) Patent No.: US 9,161,532 B2
(45) Date of Patent: *Oct. 20, 2015

(54) CINNAMALDEHYDE-ALLICIN FORMULATIONS AND METHODS OF THEIR USE

(71) Applicant: Valent BioSciences Corporation, Libertyville, IL (US)

(72) Inventors: Bala N. Devisetty, Libertyville, IL (US); Bassam Shammo, Libertyville, IL (US); Linda A. Rehberger, Libertyville, IL (US); Rebecca Dickenson, Libertyville, IL (US); Heemanshubhai K. Patel, Libertyville, IL (US); Daniel F. Heiman, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 178 days.

This patent is subject to a terminal disclaimer.

(21) Appl. No.: 13/667,598

(22) Filed: Nov. 2, 2012

(65) Prior Publication Data

US 2013/0059909 A1 Mar. 7, 2013

Related U.S. Application Data

(63) Continuation-in-part of application No. 12/580,401, filed on Oct. 16, 2009, now Pat. No. 8,334,002.

(60) Provisional application No. 61/106,191, filed on Oct. 17, 2008.

(51) Int. Cl.
*A01N 35/02* (2006.01)
*A01N 41/02* (2006.01)

(52) U.S. Cl.
CPC ............... *A01N 35/02* (2013.01); *A01N 41/02* (2013.01)

(58) Field of Classification Search
CPC ... A61K 36/54; A61K 36/8962; A01N 35/02; A01N 65/00; A01N 41/02
See application file for complete search history.

(56) References Cited

U.S. PATENT DOCUMENTS

| 4,546,108 | A | * | 10/1985 | Rout et al. ............ 514/464 |
| 4,978,686 | A | | 12/1990 | Sotome |
| 5,051,255 | A | | 9/1991 | Devidas et al. |
| 5,057,141 | A | | 10/1991 | Rodriquez-Kabana et al. |
| 5,182,207 | A | | 1/1993 | Ward et al. |
| 5,360,607 | A | | 11/1994 | Eyal et al. |
| 5,439,934 | A | | 8/1995 | Wood et al. |
| 6,231,865 | B1 | | 5/2001 | Hsu et al. |
| 6,251,951 | B1 | | 6/2001 | Emerson et al. |
| 6,750,256 | B1 | | 6/2004 | Crandall, Jr. et al. |
| 2004/0077713 | A1 | | 4/2004 | Maupin et al. |
| 2004/0087665 | A1 | | 5/2004 | Aubert et al. |
| 2006/0110472 | A1 | | 5/2006 | Miron et al. |

FOREIGN PATENT DOCUMENTS

| EP | 0 843 965 | 5/1998 |
| EP | 0 945 066 | 9/1999 |
| GB | 1 465 533 | 2/1977 |
| JP | 2004-529120 | 5/2012 |
| WO | WO 99/52359 | 10/1999 |
| WO | WO 2006/109028 | 10/2006 |

OTHER PUBLICATIONS

Y.Oka, "Nematicidal activity of essential oil components against the root-knot nematode *Meloidogyne javanica*", Nematology, 2001, vol. 3(2) pp. 159-164.
R. Pandy et al., "Essential oils as potent sources of nematicidal compounds", J. Phytopathology 148, 2000, pp. 501-502.
Park Nematicidal activity of plant essential oils and components from garlic (*Allium sativum*) and cinnamon (*Cinnamomum verum*) oils against the pine wood nematode (*Bursaphelenchus xylophilus*), 2005 Nematology vol. 7(5) pp. 767-774.
Auger et al. "Insecticidal and fungicidal potential of *Allium* substances as biofumigants", Argroindustria, 2004, vol. 3 No. 3, pp. 5-8.
Lawson et al., "Compositions, Stability, and Bioavailability of Garlic Products Used in a Clinical Trial" Journal of Agricultural Food Chemistry, 2005, 53, pp. 6254-6261.
Fujisawa et al., "Biological and Chemical Stability of Garlic-Derived Allicin", Journal of Agricultural and Food Chemistry, 2008, 56, pp. 4229-4235.
Miller (Journal of Nematology, 11(4):402-403 1979).
EESR Issued Jun. 10, 2013.
Block, "The Organosulfur Chemistry of the Genus *Allium*—Implications for the Organic Chemistry of Sulfur", Agnew. Chem. Int. Ed. Engl. 1992, 31, pp. 1135-1178.

* cited by examiner

*Primary Examiner* — Bong-Sook Baek
(74) *Attorney, Agent, or Firm* — Wood, Phillips, Katz, Clark & Mortimer

(57) ABSTRACT

The invention is directed to emulsifiable oil suspension concentrate formulations containing cinnamaldehyde (cinnamic aldehyde) and allicin that are effective in protecting plants from pests, especially nematodes, and methods of their use.

20 Claims, No Drawings

US 9,161,532 B2

CINNAMALDEHYDE-ALLICIN FORMULATIONS AND METHODS OF THEIR USE

PRIORITY

This application is a continuation-in-part to U.S. patent application Ser. No. 12/580,401, filed Oct. 16, 2009, which claims priority to U.S. Provisional Patent Application No. 61/106,191, filed Oct. 17, 2008, the entirety of each is herein incorporated by reference.

FIELD OF THE INVENTION

The present invention generally relates to cinnamaldehyde and allicin formulations that have synergistic activity against plant parasitic nematodes and other soil and plant pathogens, and methods of their use.

BACKGROUND OF THE INVENTION

Plant parasitic nematodes cause serious economic damage to many agricultural crops around the world. The nematodes in this group are microscopic worms and in general are obligate parasites of plants. They feed mostly on the roots of host plants; however, several genera are known to parasitize above-ground parts including stems, leaves and flowers as well. Almost all the plant species of economic importance are susceptible to infection by some species of nematodes. For example, root knot nematodes (RKN), (*Meloidogyne* spp.) are capable of parasitizing more than 3,000 species of crop plants.

The symptoms due to parasitic nematode injury vary widely depending on the plant host, the nematode species, the age of the plant, geographical location and climatic and external environmental conditions. In general, an overall patchy appearance of crop plants in a field is considered to be indicative of nematode infestation. More specifically, nematode injury can manifest itself, for example, as galling of the roots (abnormal swelling in the tissue due to rapid multiplication of cells in the cortical region) caused by species of root knot (*Meloidogyne* spp.) and cyst (*Heterodera* spp.). Nematodes can also be vectors of plant viruses and are also known to induce disease complexes, predisposing plants to infection by other plant pathogenic fungi and bacteria.

Chemical nematicides, either soil fumigants or non-fumigants, have been in use for many years and are among the few feasible options for countering nematodes. At present, repeated applications of synthetic chemicals to the field are required prior to planting the crop. These chemicals are extremely toxic to non-target organisms besides nematodes and many of them may pose serious threats to the environment. Because of these downfalls, there is a need for effective nematicides with low toxicity.

Plant essential oils, which do not present any known risk to humans or to the environment, are qualified for an exemption as minimum risk pesticides and are listed in 40 C.F.R. §152.25 (b). However, high volatility, phytotoxicity and low water solubility of some oils have limited their use in crop protection.

The nematicidal activity of cinnamaldehyde is known. For example, ProGuard® 30% Cinnamaldehyde Plowable Insecticide, Miticide and Fungicide (U.S. Pat. Nos. 6,750,256 B1 and 6,251,951 B1) demonstrates that cinnamaldehyde has nematicidal activity in the presence of a 2% Tween 80 and 6% NaHCO$_3$. However, a disadvantage of this commercial product is that it contains the chemical preservative o-phenylphenol. Further, cinnamaldehyde may result in plant phytotoxicity especially when used at rates high enough to provide nematode protection (500 ppm and above).

Garlic extract may be known to control nematodes, however, the cost of garlic extract is too prohibitive to be a practical solution to nematode infestation of a field. Further, garlic extract formulations are often aqueous and the stability of the active components in aqueous preparations is questionable.

U.S. Pat. No. 4,978,686 ("the '686 patent") suggests a composition comprising cinnamaldehyde, an antioxidant, an emulsifier, and water. However, the '686 patent does not teach or suggest the use of cinnamaldehyde with ailicin formulated together to provide superior nematicdial activity.

Accordingly, there is a need to develop a safe, easy-to-use, cost-effective delivery system, so as to improve the biological effectiveness of plant essential oils/plant extracts, for agricultural applications. There is especially need for an effective and environmentally safe nematicide formulation.

SUMMARY OF THE INVENTION

The present invention generally relates to emulsifiable oil suspension concentrate formulations suitable for agricultural use that comprise liquid cinnamaldehyde (also known as cinnamic aldehyde), allicin in fine powder form, a solvent selected from the group consisting of corn oil, cotton seed oil, paraffinic oil, methyl soyate, canola seed oil, and esters thereof, an emulsifier, a solvent, a rheological modifier selected from the group consisting of organophillic hectorite clay, modified bentonite clay, and castor oil derivatives (hydrogenated and/or organically modified), a polar additive, and a non-ionic surfactant.

The invention further relates to methods for protecting a plant from nematodes that includes applying an effective amount of the claimed formulations to the locus, soil, or seeds of the plant.

DETAILED DESCRIPTION OF THE INVENTION

In one embodiment, the invention is directed to agricultural formulations comprising cinnamaldehyde, allicin, a solvent selected from the group consisting of soybean oil, corn oil, cotton seed oil, paraffinic oil, methyl soyate, canola seed oil, isoparaffinic oil, and esters thereof, an emulsifier, a rheological modifier selected from the group consisting of organophillic hectorite clay, modified bentonite clay, and castor oil derivatives (hydrogenated and/or organically modified), a polar additive; and a non-ionic surfactant.

The percentage following allicin found throughout the application and in the example refers to the amount of allicin present in the technical product in a % w/w. Those of skill in the art are aware that the "(10%)" following allicin indicates the amount of the allicin in the technical material used in the formulation. Those of skill in the art are also aware that other technical allicin products may be used with various concentrations of allicin present without departing from the nature of the invention.

In a further embodiment, the formulation may contain from about 10 to 20% wt./wt. of cinnamaldehyde. Preferably, the formulation may contain about 20% wt./wt. of cinnamaldehyde.

In yet another embodiment, the formulation may contain from about 1 to 15% wt./wt. of allicin (10%). Preferably, the formulation may contain about 20% wt./wt. of allicin (10%).

In another embodiment, the formulation may contain from about 50 to 80% wt./wt. of solvent. Preferably, the formulation may contain about 50 to 60% wt./wt. of solvent, and more preferably, about 58% wt./wt. of a solvent.

In an embodiment, the formulation may contain from about 3 to 12% wt./wt. of an emulsifier. Preferably, the formulation may contain about 5% wt./wt. of an emulsifier.

In yet another embodiment, the formulation may contain from about 0.8 to 2.0% wt./wt. of a rheological modifier. Preferably, the formulation may contain about 1.6% wt./wt. of a rheological modifier.

In a further embodiment, the formulation may contain from about 0.5 to 3.0% wt./wt. of a polar additive. Preferably, the formulation may contain about 1% wt./wt. of a polar additive.

In another embodiment, the formulation may contain from about 0.5 to 2.0% wt./wt. of a non-ionic surfactant. Preferably, the formulation may contain about 0.5% wt./wt. of a non-ionic surfactant.

In a preferred embodiment, the formulation contains: from about 10 to 20% wt./wt. of cinnamaldehyde; from about 10 to 40% wt./wt. of allicin (10%); from about 50 to 80% wt./wt. a the solvent selected from the group consisting of corn oil, cotton seed oil, paraffinic oil, methyl soyate, canola seed oil, and esters thereof; from about 3 to 12% wt./wt. of the emulsifier; from about 0.8 to 2.0% wt./wt. of the rheological modifier selected from the group consisting of organophillic hectorite clay, modified bentonite clay, and castor oil derivatives (hydrogenated and/or organically modified); from about 0.5 to 3.0% wt./wt. of the polar additive; and from about 0.5 to 2.0% wt./wt. of the non-ionic surfactant.

In yet another embodiment, the invention is directed to methods for protecting a plant from nematodes comprising applying an effective amount of the formulations of the present invention to the plant.

In a further embodiment, the invention is directed to methods for applying the formulations of the present invention either prior to planting or following planting, neat or diluted in water or other agricultural carriers, and to the plant or soil either by spray equipment or by irrigation equipment.

In another embodiment, the formulations of the present invention are tank-mixed with pesticides and/or fertilizer solutions for enhanced pesticidal activity or for economic reasons prior to application.

These representative embodiments are in no way limiting and are described solely to illustrate some aspects of the invention.

The phrase "protecting a plant" means controlling the growth of pathogens, which may involve killing the pathogen and/or slowing or arresting its proliferation, or providing a confusing or repellent action so that the pathogenic organism is unable to come in contact with the plant and attack it.

Representative pathogens include, but are not limited to, nematodes, fungal pathogens *Pythium, Rhizoctonia, Sclerotinia*, insect pests and other pests.

The trade names used herein are used to describe a type of component with specific chemistries. When a trade name is used herein, a component with the same of very similar chemistry may be suitable unless indicated otherwise.

The terms "composition" and "emulsifiable oil suspension concentrate formulation" and "formulation" are used interchangeably throughout the application.

As used herein, all numerical values relating to amounts, weight percentages and the like, are defined as "about" or "approximately" each particular values plus or minus 10% (±10%). For example, the phrase "greater than 0.1%" is to be understood as encompassing values greater than 0.09%. Therefore, amounts within 10% of the claimed values are encompassed by the scope of the invention.

The percentages of the components in the formulations and comparative formulations are listed by weight percentage.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the active agents and excipients of the invention, may be made without departing from the spirit and scope hereof.

The following examples are offered by way of illustration only, not to limit the scope of this invention, as represented by the claims list attached herein.

EXAMPLE

Example 1

The formulations in Tables 1 and 2 (below) may be made, for example, by the following process:

A gel concentrate may be first prepared by combining under high shear a solvent, a rheological additive, a polar additive and an emulsifier. Then, additional solvent may be charged in a vessel of suitable size and equipped with a variable speed mixer/agitator. The gel concentrate may be then added and mixed until it is homogeneously dispersed. The cinnamaldehyde may be dissolved in a solvent and then charged and mixed. The surfactants may be then added and mixed. The allicin (10%) may be slowly charged while mixing under high shear and mixed until the formulation is homogeneous.

TABLE 1

Improved Allicin and Cinnamaldehyde Formulations with Various Solvent Carriers

| No. | Component Formulation ID | % wt./wt. | | | | | |
|---|---|---|---|---|---|---|---|
| | | 1AA | 1AB | 1AC | 1AD | 1AE | 1AF |
| 1 | Corn Oil | 57.74 | — | — | — | — | — |
| 2 | Cotton Seed Oil | — | 57.74 | — | — | — | — |
| 3 | Paraffinic Oil (Sunspray 6N) | — | — | 57.74 | — | — | — |
| 4 | Methyl Soyate | — | — | — | 57.74 | — | — |
| 5 | Canola Seed Oil | — | — | — | — | 57.74 | — |
| 6 | Isoparaffinic Oil | — | — | — | — | — | 57.74 |
| 7 | Cinnamaldehyde (98.5%) | 14.20 | 14.20 | 14.20 | 14.20 | 14.20 | 14.20 |
| 8 | Allicin (10%) | 20.00 | 20.00 | 20.00 | 20.00 | 20.00 | 20.00 |
| 9 | Organophilic Hectorite Clay | 1.60 | 1.60 | 1.60 | 1.60 | 1.60 | 1.60 |
| 10 | Polyol fatty acid esters and polyethoxylated derivatives thereof: | 5.00 | 5.00 | 5.00 | 5.00 | 5.00 | 5.00 |

TABLE 1-continued

Improved Allicin and Cinnamaldehyde Formulations with Various Solvent Carriers

| No. | Component Formulation ID | % wt./wt. | | | | | |
|---|---|---|---|---|---|---|---|
| | | 1AA | 1AB | 1AC | 1AD | 1AE | 1AF |
| 11 | Propylene Carbonate Jeffsol AG1555 (Huntsman Corp.) | 0.96 | 0.96 | 0.96 | 0.96 | 0.96 | 0.96 |
| 12 | Polysorbate 20 (Tween 20) | 0.50 | 0.50 | 0.50 | 0.50 | 0.50 | 0.50 |
| | Total | 100.0 | 100.0 | 100.0 | 100.0 | 100.0 | 100.0 |

TABLE 1B

Improved Allicin and Cinnamaldehyde Formulations With Various Rheological Additives

| No. | Component Formulation ID | % wt./wt. | | | | | |
|---|---|---|---|---|---|---|---|
| | | 1BA | 1BB | 1BC | 1BD | 1BE | 1BF |
| 1 | Soybean Oil | 57.74 | 57.74 | 57.74 | — | — | — |
| 2 | Isoparaffinic Oil | — | — | — | — | 57.74 | 57.74 |
| 3 | Paraffinic Oil (Sunspray 6N) | — | — | — | 57.74 | — | — |
| 4 | Cinnamaldehyde (98.5%) | 14.20 | 14.20 | 14.20 | 14.20 | 14.20 | 14.20 |
| 5 | Allicin (10%) | 20.00 | 20.00 | 20.00 | 20.00 | 20.00 | 20.00 |
| 6 | Tixogel VP-V (Quaternium -90 Bentonite) | — | — | — | — | — | 1.60 |
| 7 | Rheocin (hydrogenated castor oil derivative) | — | — | — | — | 1.60 | — |
| 8 | Sucragel AOF (*Prunus Amygdalus Dulcis* Oil & Glycerine & Aqua & Sucrose Laurate) | — | 1.60 | — | — | — | — |
| 9 | Tixogel VZ-V (Stearalkonium Bentonite) | 1.60 | — | — | — | — | — |
| 10 | Thixtrol ST (Organically modified Castor oil derivative) | — | — | — | 1.60 | — | — |
| 11 | Bentone 27V (Organically modified hectorite clay) | — | — | 1.60 | — | — | — |
| 12 | Polyol fatty acid esters and polyethoxylated derivatives thereof: | 5.00 | 5.00 | 5.00 | 5.00 | 5.00 | 5.00 |
| 13 | Propylene Carbonate Jeffsol AG1555 (Huntsman Corp.) | 0.96 | 0.96 | 0.96 | 0.96 | 0.96 | 0.96 |
| 14 | Polysorbate 20 (Tween 20) | 0.50 | 0.50 | 0.50 | 0.50 | 0.50 | 0.50 |
| | Total | 100.0 | 100.0 | 100.0 | 100.0 | 100.0 | 100.0 |

The formulations in Tables 1 and 2 may be subjected to efficacy evaluations using standard greenhouse bioassays to prove that they effectively control galling caused by root knot nematodes or other pests. Examples of appropriate standard greenhouse bioassays are disclosed, for example, in U.S. patent application Ser. No. 12/580,401. Formulations of the present invention have the potential to replace environmentally hazardous synthetic nematicides.

The invention claimed is:

1. A nematicidal formulation suitable for agricultural use consisting of:
   (a) cinnamaldehyde;
   (b) allicin (10%);
   (c) a solvent selected from the group consisting of soybean oil, corn oil, cotton seed oil, paraffinic oil, methyl soyate, canola seed oil, and esters thereof;
   (d) an emulsifier;
   (e) a rheological modifier selected from the group consisting of modified bentonite clay and hydrogenated and/or organically modified castor oil derivatives;
   (f) a polar additive which is propylene carbonate; and
   (g) a non-ionic surfactant.

2. The formulation of claim 1, wherein the cinnamaldehyde is from about 10 to 20% wt./wt. of the total formulation.

3. The formulation of claim 1, wherein the allicin (10%) is from about 1 to 15% wt./wt. of the total formulation.

4. The formulation of claim 1, wherein the solvent is from about 50 to 80% wt./wt. of the total formulation.

5. The formulation of claim 1, wherein the emulsifier is from about 3 to 12% wt./wt. of the total formulation.

6. The formulation of claim 1, wherein the rheological modifier is from about 0.8 to 2.0% wt./wt. of the total formulation.

7. The formulation of claim 1, wherein the polar additive is from about 0.5 to 3.0% wt./wt. of the total formulation.

8. The formulation of claim 1, wherein the non-ionic surfactant is from about 0.5 to 2.0% wt./wt. of the total formulation.

9. The formulation of claim 1, consisting of:
   (a) from about 10 to 20% wt./wt. of cinnamaldehyde;
   (b) from about 10 to 40% wt./wt. of allicin (10%);
   (c) from about 50 to 80% wt./wt. of the solvent selected from the group consisting of soybean oil, corn oil, cotton seed oil, paraffinic oil, methyl soyate, canola seed oil, and esters thereof;
   (d) from about 3 to 12% wt./wt. of the emulsifier;
   (e) from about 0.8 to 2.0% wt./wt. of the rheological modifier selected from the group consisting of modified bentonite clay and hydrogenated and/or organically modified castor oil;

(f) from about 0.5 to 3.0% wt./wt. of the polar additive; and
(g) from about 0.5 to 2.0% wt./wt. of the non-ionic surfactant.

10. A nematicidal formulation suitable for agricultural use consisting of:
(a) cinnamaldehyde;
(b) allicin (10%);
(c) a solvent selected from the group consisting of corn oil, cotton seed oil, paraffinic oil, methyl soyate, canola seed oil, and esters thereof;
(d) an emulsifier;
(e) a rheological modifier selected from the group consisting of organophillic hectorite clay, modified bentonite clay, and hydrogenated and/or organically modified castor oil derivatives;
(f) a polar additive which is propylene carbonate; and
(g) a non-ionic surfactant.

11. A method of protecting a plant from nematodes comprising applying an effective amount of the formulation of claim 1 to soil or a plant.

12. The method of claim 11, wherein the formulation is applied either prior to planting or following planting, neat or diluted in water or other agricultural carriers and to the plant or soil either by spray equipment or by irrigation equipment.

13. The method of claim 11, wherein the formulation is tank-mixed with pesticides and/or fertilizer solutions for enhanced pesticidal activity or for economic reasons.

14. The formulation of claim 10, wherein the cinnamaldehyde is from about 10 to 20% wt./wt. of the total formulation.

15. The formulation of claim 10, wherein the allicin (10%) is from about 1 to 15% wt./wt. of the total formulation.

16. The formulation of claim 10, wherein the solvent is from about 50 to 80% wt./wt. of the total formulation.

17. The formulation of claim 10, consisting of:
(a) from about 10 to 20% wt./wt. of cinnamaldehyde;
(b) from about 10 to 40% wt./wt. of allicin (10%);
(c) from about 50 to 80% wt./wt. of the solvent selected from the group consisting of corn oil, cotton seed oil, paraffinic oil, methyl soyate, canola seed oil, and esters thereof;
(d) from about 3 to 12% wt./wt. of the emulsifier;
(e) from about 0.8 to 2.0% wt./wt. of the rheological modifier selected from the group consisting of organophillic hectorite clay, modified bentonite clay, and hydrogenated and/or organically modified castor oil derivatives;
(f) from about 0.5 to 3.0% wt./wt. of the polar additive; and
(g) from about 0.5 to 2.0% wt./wt. of the non-ionic surfactant.

18. A method of protecting a plant from nematodes comprising applying an effective amount of the formulation of claim 10 to soil or a plant.

19. The method of claim 18, wherein the formulation is applied either prior to planting or following planting, neat or diluted in water or other agricultural carriers and to the plant or soil either by spray equipment or by irrigation equipment.

20. The method of claim 18, wherein the formulation is tank-mixed with pesticides and/or fertilizer solutions for enhanced pesticidal activity or for economic reasons.

* * * * *